(12) United States Patent
Aliota

(10) Patent No.: US 12,364,571 B2
(45) Date of Patent: Jul. 22, 2025

(54) ADJUSTABLE RADIOGRAPHY TEMPLATE DEVICES

(71) Applicant: Jonathan Aliota, Houston, TX (US)

(72) Inventor: Jonathan Aliota, Houston, TX (US)

(73) Assignee: Jonathan Aliota, Houston, TX (US)

( * ) Notice: Subject to any disclaimer, the term of this patent is extended or adjusted under 35 U.S.C. 154(b) by 639 days.

(21) Appl. No.: 17/651,193

(22) Filed: Feb. 15, 2022

(65) Prior Publication Data

US 2022/0257281 A1    Aug. 18, 2022

Related U.S. Application Data

(60) Provisional application No. 63/150,218, filed on Feb. 17, 2021.

(51) Int. Cl.
*A61B 90/00* (2016.01)

(52) U.S. Cl.
CPC ........ *A61B 90/39* (2016.02); *A61B 2090/376* (2016.02); *A61B 2090/3908* (2016.02); *A61B 2090/3916* (2016.02); *A61B 2090/395* (2016.02); *A61B 2090/3966* (2016.02)

(58) Field of Classification Search
CPC .............. A61B 90/39; A61B 2090/376; A61B 2090/3908; A61B 2090/3916; A61B 2090/395; A61B 2090/3966
See application file for complete search history.

(56) References Cited

U.S. PATENT DOCUMENTS

| | | | | |
|---|---|---|---|---|
| 6,097,978 | A | * | 8/2000 | Demarais .................. A61F 2/07 378/163 |
| 11,426,137 | B1 | * | 8/2022 | Simms ...................... A61B 6/58 |
| 2002/0064478 | A1 | * | 5/2002 | Davis ........................ A61L 2/26 422/26 |

* cited by examiner

*Primary Examiner* — Chih-Cheng Kao
(74) *Attorney, Agent, or Firm* — Fish & Richardson P.C.

(57) ABSTRACT

Some adjustable radiography template devices include a base member including one or more first radiopaque (RO) markers; an arm pivotally coupled to the base member; and a marker member slidably coupled to the arm and including a second RO marker. Some methods of using adjustable radiography template devices include locating a base member on a skin of a patient; locating a marker member of on the skin of the patient; and while a second RO marker is aligned with a puncture site of the blood vessel, marking a location of the second RO marker on the skin of the patient.

20 Claims, 8 Drawing Sheets

ADJUSTABLE RADIOGRAPHY TEMPLATE DEVICES

CROSS-REFERENCE TO RELATED APPLICATIONS

This application claims the benefit of U.S. Provisional Application No. 63/150,218, filed Feb. 17, 2021, the contents of which are incorporated herein by reference.

BACKGROUND

1. Technical Field

This document relates to adjustable radiography template devices used, e.g., during and after invasive cardiology procedures.

2. Background Information

Invasive cardiologists or another trained clinician (collectively hereinafter "clinician") commonly perform procedures within the circulatory system of the patient (e.g., coronary arteries, cerebrovascular arteries and other blood vessels). Oftentimes, this involves creating a small puncture in the skin of a patient (e.g., through the skin above the femoral artery, usually termed "femoral access") and inserting devices such as a sheath through the puncture and then into a blood vessel. While radial artery and other percutaneous approaches are sometimes used, femoral access remains a main access point to the circulatory system of the patient for percutaneous/invasive radiology and cardiology procedures.

A needle and/or sheath is inserted through the small skin entry site until it punctures and passes into a blood vessel of the patient (e.g., an artery or vein). In this way, the sheath is an access point for the clinician to gain access to the circulatory system of the patient. Often the clinician inserts the sheath into the femoral artery or femoral vein in the "groin area" of the patient which is the skin above the bony head of the femur where the femoral artery and vein run more superficially toward the surface.

After the procedure, the clinician extracts the sheath and must "close" the small puncture. The clinician estimates the location of the access point where the sheath entered the blood vessel. During recovery, pressure is applied for an extended period of time to the estimated location of this blood vessel access point to help the puncture of the vessel to close, known as achieving "hemostasis."

However, the exact location of the subcutaneous access point to the blood vessel is difficult to determine and, as a result, sometimes the vessel does not become completely closed (e.g., healed) as a result of the pressure that is applied. In such a case, adverse effects such as bleeding, hematomas, pseudo-aneurysms, and/or other complications may arise, requiring extensive medical attention, longer hospital stays, prolonged bleeding and, in extreme cases, death of the patient.

SUMMARY

This document describes adjustable radiography template devices and methods for using adjustable radiography template devices. For example, this document describes adjustable radiography template devices for use during and after invasive cardiology procedures.

After an invasive cardiology procedure is performed on a patient, proper closure of the puncture site of the blood vessel is necessary. The likelihood of a proper closure is improved when pressure is applied accurately at the location of the blood vessel puncture site. To be clear, the pressure must be applied to the location where the sheath entered the blood vessel (the vessel puncture site), which typically does not coincide with the location of the patient's skin incision.

However, after the introducer sheath is removed, clinicians often have difficulty determining precisely where the subcutaneous vessel puncture site is located. In some cases, the vessel may be a few millimeters (e.g., 5 mm) to a few centimeters (e.g., 4 cm) below the patient's skin surface. In some cases, the angle between the skin puncture site and the blood vessel puncture site can be low (e.g., approximately parallel to the skin's surface) or steep (e.g., approximately perpendicular to the skin's surface, or any angle between). This variance in angle makes it more difficult to predict where the blood vessel puncture site is located based solely on where the skin puncture site is located.

In addition, excess skin, fat tissue, and skeletal structure of each patient varies, further adding to the complexity of identifying the precise location of the vessel puncture site. Usually, these sheaths are removed in a holding area, so the clinician also does not typically have the use of real-time radiography in the moments before sheath extraction. As a result, after the sheath is removed, clinicians have difficulty determining the exact location where the pressure should be applied, resulting in less optimal closure rates of the puncture site.

As previously noted, if the vessel puncture site is not closed property, then undesired levels of bleeding can occur. In some cases, it could take 30-45 minutes before the bleeding is noticeable by the patient (e.g., by the development of a hematoma). Clinicians typically use a three finger hold (two figures above vessel puncture site and one finger below the vessel puncture site in case the puncture sites begins to bleed backwards) to apply pressure to the vessel puncture site. Some clinicians sometimes even apply pressure with their whole fist if the bleeding cannot be controlled.

This disclosure describes adjustable radiography template devices that are used for marking the patient's skin to accurately identify the location of the subcutaneous vessel puncture site. With the location of the vessel puncture site accurately indicated on the patient's skin, clinicians can apply pressure to the correct area of the patient, thereby increasing the likelihood of successful closure of the vessel puncture site.

In a first aspect, an adjustable radiography template device includes a base member including one or more first radiopaque (RO) markers, an arm pivotally coupled to the base member, and a marker member slidably coupled to the arm and including a second RO marker.

The adjustable radiography template device may optionally include one or more of the following features.

In some implementations, the base member, the arm, and the marker member are radio transparent. In some implementations, the base member, the arm, and the marker member are less radiopaque than the one or more first RO markers and the second RO marker. In some implementations, the one or more first RO markers define a radiopaque arc. In some cases, the arm is pivotally coupled to the base member via a pivot axis located at a radial center of the radiopaque arc.

In some implementations, the marker member is slidably coupled to the arm via a longitudinal track of the arm. In some implementations, the base member comprises one or more edges defining an arc. In some cases, the one or more edges of the base member are concentric with a radiopaque arc defined by the one or more first RO markers.

In some implementations, the one or more first RO markers are arranged in a semi-circular portion of the base member. In some cases, an outer diameter of the semi-circular portion is concentric with a radiopaque arc defined by the one or more first RO markers. In some cases, the arm is pivotally coupled to the base member at a radial center of the semi-circular portion. In some implementations, the arm is pivotally coupled to the base member at a radial center of the base member.

In some implementations, the base member comprises one or more openings passing through the base member. In some implementations, an entire side of the base member is flat. In some implementations, the one or more first RO markers and the second RO marker are copper (or other radio opaque metal) wires.

In some implementations, a length of the arm is equal to a radial outer dimension of the base member. In some implementations, the marker member is removable from the arm via an end of a longitudinal track of the arm. In some implementations, the marker member is positionable along the arm by frictional engagement between the marker member and the arm. In some implementations, the adjustable radiography template device is sterile and contained in a sterile packaging.

In some implementations, the adjustable radiography template device is a single use device. In some implementations, the adjustable radiography template device is sterilizable.

In a second aspect, an adjustable radiography template device includes a base member defining comprising one or more first radiopaque (RO) markers defining a radiopaque arc and one or more edges defining an arc concentric with the radiopaque arc; an arm pivotally coupled to the base member at a pivot axis, the pivot axis located at a radial center of the radiopaque arc; and a marker member slidably coupled to the arm via a longitudinal track of the arm, the marker member comprising a second RO marker.

The adjustable radiography template device may optionally include one or more of the following features.

In some implementations, the base member, the arm, and the marker member are less radiopaque than the one or more first RO markers and the second RO marker. In some implementations, the one or more first RO markers and the second RO marker are copper wires. In some implementations, the marker member is positionable along the arm by frictional engagement between the marker member and the arm.

In a third aspect, a method for using an adjustable radiography template device includes locating a base member of an adjustable radiography template device on a skin of a patient such that one or more first radiopaque (RO) markers of the base member are aligned, as observed in an x-ray image, with a head of a femoral bone of the patient; locating a marker member of the adjustable radiography template device on the skin of the patient such that a second RO marker on the marker member is aligned, as observed in the x-ray image, with a puncture site of an blood vessel of the patient; and while the second RO marker is aligned with the puncture site of the blood vessel, marking a location of the second RO marker on the skin of the patient.

The method of using the adjustable radiography template device may optionally include one or more of the following features.

In some implementations, locating the base member of the adjustable radiography template device on the skin of the patient comprises guiding an alignment of the one or more first RO markers with the head of the femoral bone of the patient using fluoroscopy. In some implementations, locating the marker member of the adjustable radiography template device on the skin of the patient comprises guiding an alignment of the second RO marker with the puncture site of the blood vessel of the patient using fluoroscopy.

In some implementations, the method includes, while the one or more first RO markers are aligned with the head of the femoral bone of the patient, marking a location of the base member on the skin of the patient. In some cases, marking the location of the base member on the skin of the patient comprises marking one or more arcs on the skin of the patient using one or more edges of the base member as a guide. In some cases, marking the location of the base member on the skin of the patient comprises marking one or more arcs through one or more openings in the base member. In some cases, each of the one or more arcs are concentric and radially outward from the one or more first RO markers of the base member. In some cases, each of the one or more arcs are concentric to a pivot axis of an arm that comprises the marker member.

In some implementations, locating the marker member of the adjustable radiography template device on the skin of the patient comprises sliding the marker member along a longitudinal axis of an arm of the adjustable radiography template device. In some implementations, locating the marker member of the adjustable radiography template device on the skin of the patient comprises pivoting the marker member with respect to the base member of the adjustable radiography template device. In some implementations, the method includes capturing the x-ray image using fluoroscopy.

In some implementations, the method includes capturing the x-ray image using an angiography medical imaging technique. In some implementations, the one or more first RO markers are a wire defining a radiopaque arc. In some implementations, the method includes inserting a sheath into the blood vessel of the patient. In some implementations, the method includes removing the sheath from the blood vessel of the patient. In some implementations, the method includes applying pressure to the skin at the marked location of the marker member. In some cases, applying pressure to the skin comprises applying pressure to the skin for at least 15 minutes. In some implementations, applying the pressure to the skin incudes applying pressure to the skin in a direction towards the location such that the puncture site of the blood vessel is compressed between the a source of the applied pressure and the head of the femoral bone of the patient.

Particular embodiments of the subject matter described in this document can be implemented to realize one or more of the following advantages.

As described above, an adjustable radiography template device increases the likelihood of proper closure of the puncture site. In these cases, recovery time of the patient and a risk of complications can also be reduced due to the proper closure.

An adjustable radiography template device that is inexpensive to manufacture means that is can be provided as a single use device. In these cases, clinicians do not need to sanitize the devices after use since the device can simply be discarded.

An adjustable radiography template device that includes RO markers allows the clinician to guide the RO markers in position while referring to an x-ray image. Furthermore, since the RO markers are mechanically connected to guiding surfaces of the adjustable radiography template device, once the RO markers are in position, the clinician can use the guiding surfaces as a stencil to mark the skin of the patient.

An adjustable radiography template device with an arm that can pivot about a large (e.g., 180 degree or 360 degree) axis and a marker member that can slide along a longitudinal axis of the covers nearly all possible scenarios of patients encountered during invasive cardiology procedures. In this way, a single adjustable radiography template device can be used in nearly all patient scenarios.

An adjustable radiography template device enables a clinician to mark the locations where pressure needs to be applied. For examples, without an adjustable radiography template device, a clinician would need to constantly look up at monitor and look back at the skin of the patient to figure out where to mark the skin. If marking the skin during this process, the patient's skin is marked with a series of zigzag lines and is generally unrecognizable to the clinician who drew it, let alone the clinician that will apply pressure. In this way, the adjustable radiography template device enables the clinician to minimize the number of markings drawn on the patient, which simplifies the process of marking the patient and is less confusing for the clinician who will apply pressure.

The details of one or more implementations of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes adjustable radiography template devices and methods for using adjustable radiography template devices. For example, this document describes adjustable radiography template devices for use during invasive cardiology procedures. An adjustable radiography template device can be used by clinicians to mark a surface of the patient's skin. The markings are used to identify the location of a subcutaneous blood vessel puncture site such that pressure can be applied to the correct location of the patient's skin, thereby increasing the likelihood of successful closure of the vessel puncture site.

Figure 1:
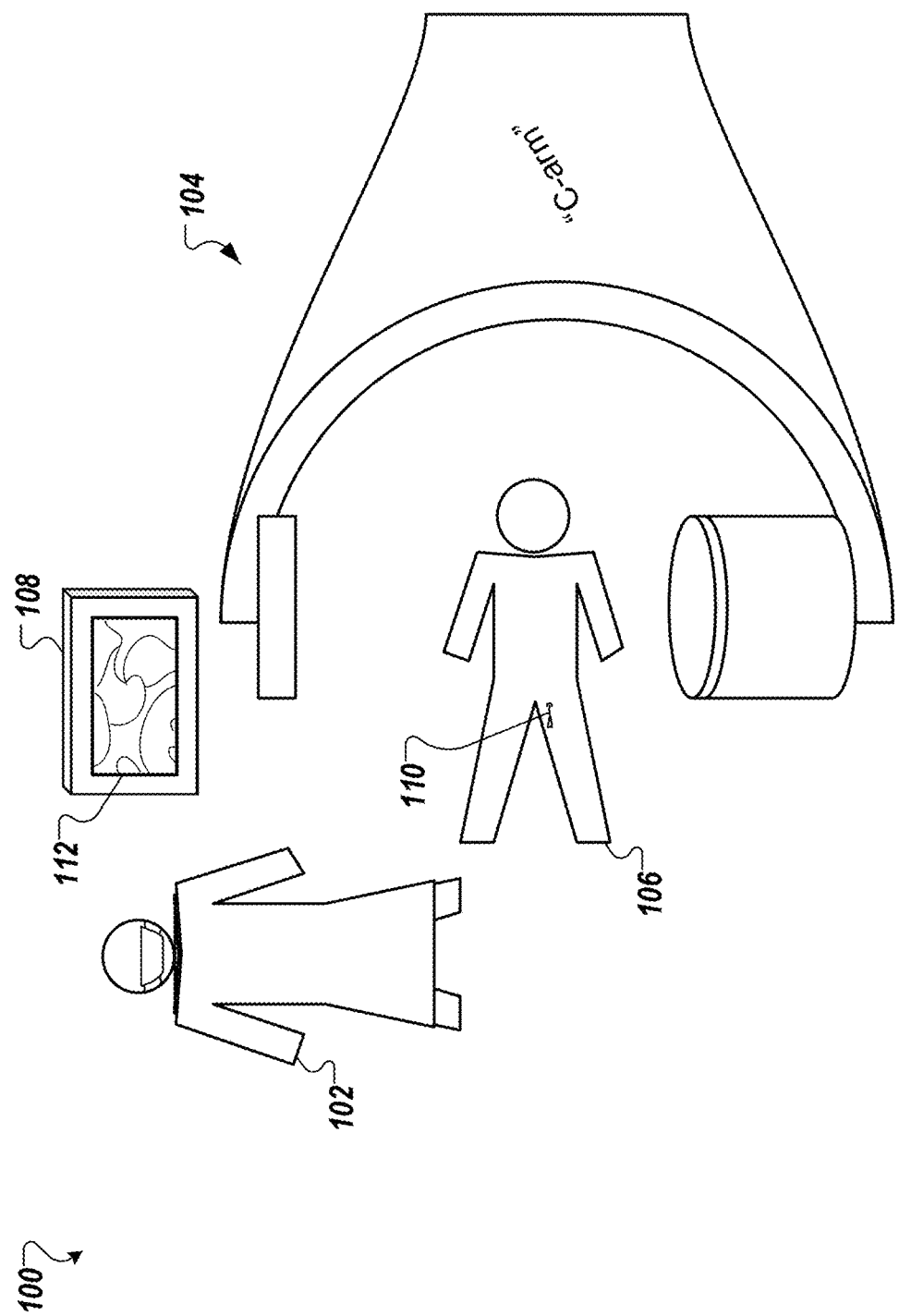
FIG. 1 shows a surgical environment for performing an invasive vascular medical procedure.

FIG. 1 shows an example surgical environment 100 for performing an invasive vascular procedure on a patient 106. The environment 100 includes a fluoroscopy system 104 with a "C-arm." The fluoroscopy system 104 is capable of acquiring x-ray images of the patient 106 while the patient 106 is undergoing an invasive cardiology procedure by a clinician 102. The fluoroscopy system 104 includes a display 108 capable of displaying the acquired x-ray images to the clinician 102 during the procedure. In some examples, the displayed image is an angiogram or a fluoroscopy image.

In the example scenario shown in FIG. 1, the patient 106 is undergoing an invasive interventional procedure to insert a stent via the patient's femoral artery. To gain access to the femoral artery, the clinician 102 makes an incision in the patient's skin in the groin area of the patient 106. Once a skin incision has been made, the clinician 102 makes a second incision into the femoral artery (e.g., a puncture site of the artery) of the patient 106 using the same puncture needle. The clinician 102 inserts a sheath 110 into the patient 106 and into the femoral artery via the puncture site to aid inserting the stent into location. The clinician 102 can confirm the locations of the sheath 110 and the stent (not shown) location using the x-ray images from the fluoroscopy system 104 presented on the display 108.

Figure 2A:
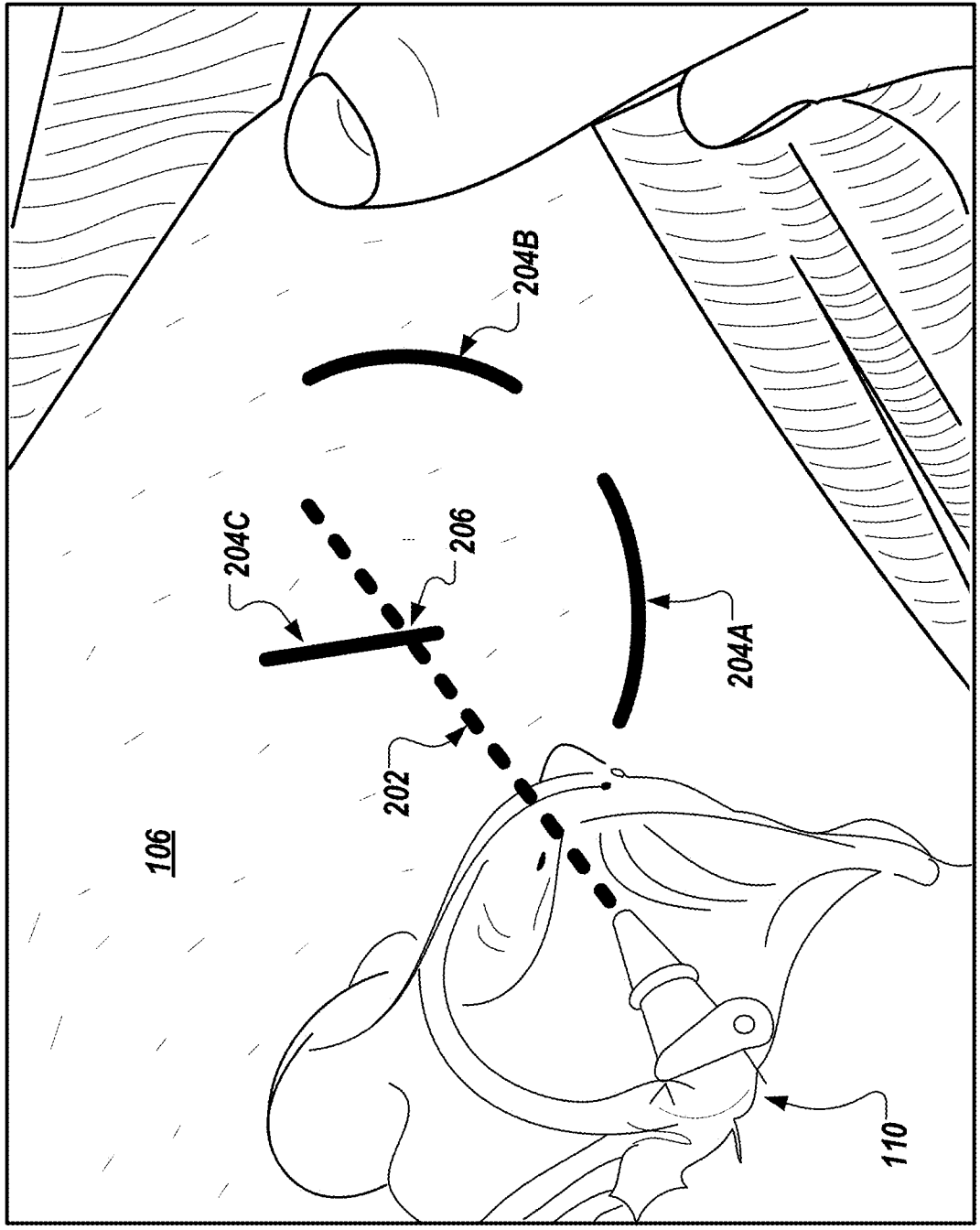
FIGS. 2A and 2B show a patient with a sheath inserted into the patient during an invasive vascular medical procedure.
Figure 2B:
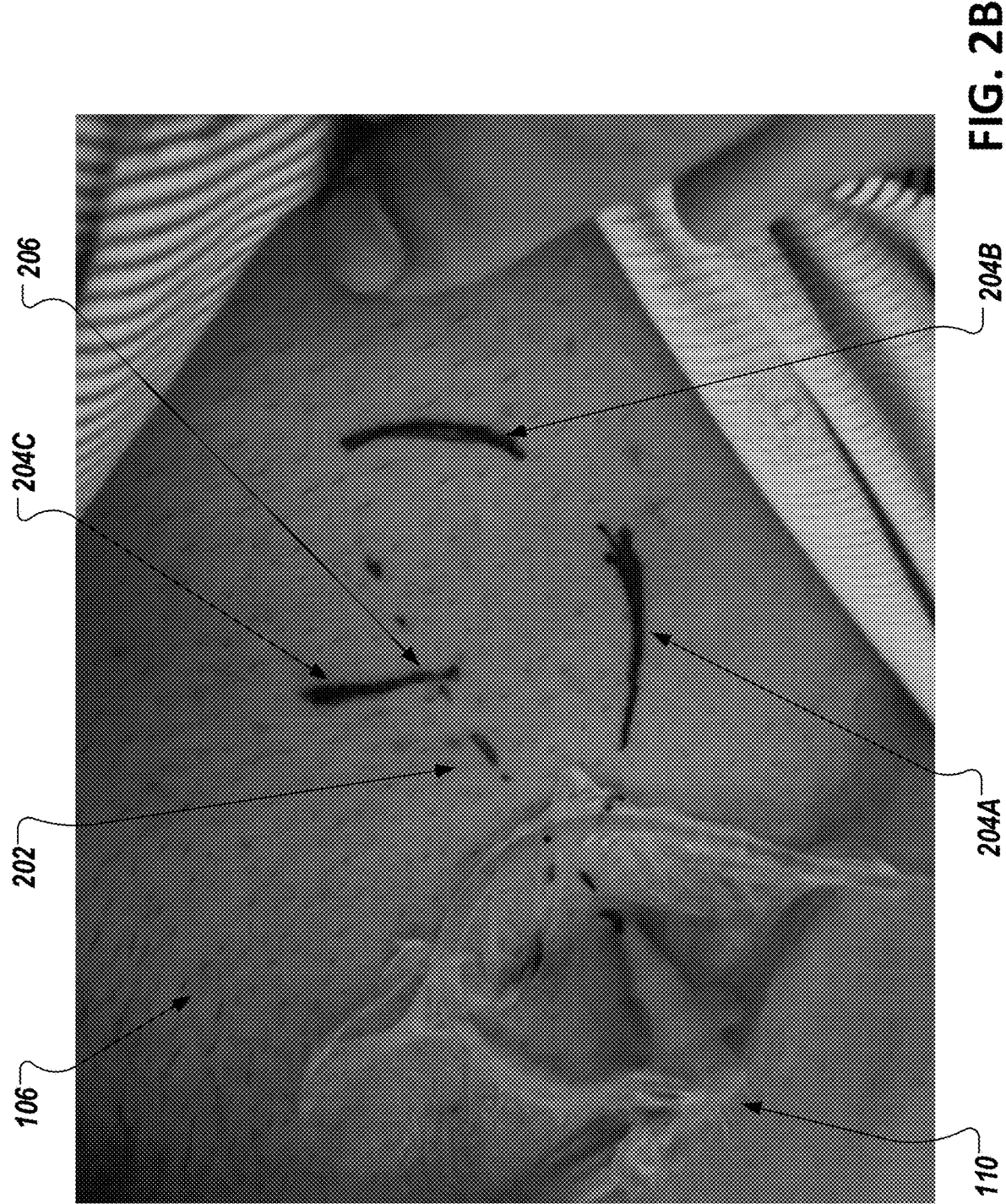

FIGS. 2A and 2B show the patient 106 with the sheath 110 inserted into the groin area of the patient 106 during an invasive interventional surgical procedure such as the procedure described with reference to FIG. 1. A marking 202 (e.g., a line, arc, etc.) drawn on the skin of the patient 106 shows the approximate position of the sheath 110 underneath the skin. In some examples, the clinician 102 draws the marking 202 on the skin of the patient 106 while referring to an x-ray image shown on the display 108.

FIGS. 2A and 2B also show additional markings 204A, 204B, 204C (generally "markings 204") on the skin of the patient 106. In some examples, the clinician 102 draws the markings 204 using an adjustable radiography template device described in further detail with reference to FIGS. 3A and 3B. Markings 204A, 204B indicate the location of the rim (outer profile) of the head of the head of the femoral bone of the patient 106 and marking 204C represents the location of the femoral artery that includes the puncture site. An intersection point 206 between the marking 202 and the marking 204C represents the location of where the sheath 110 is inserted in the artery. However, in some examples, marking 204C is sufficient to convey the location of the vessel puncture site and the marking 202 and/or the intersection point 206 is not explicitly drawn on the patient's skin.

The location of the rim of the head of the femoral bone of the patient 106 is important because the likelihood of proper closure of the vessel puncture site increases when pressure is applied in a direction towards the head of the femoral bone. In other words, when pressure is applied to the vessel puncture site such that the femoral artery is compressed between the source of the applied pressure (e.g., the clinician's hand) and the head of the femoral bone, the likelihood of proper closure of the vessel puncture site is increased. Furthermore, since the head of the femoral bone of the patient 106 includes a circular profile observable by the clinician 102 via the x-ray image on the display 108, the rim markings 204A, 204B of the head of the femoral bone provide a repeatable way to represent the location of the head of the femoral bone of the patient 106 on the skin of the patient 106.

The location of the puncture site of the blood vessel is important because this is where the pressure is preferably applied to increase the likelihood of proper closure. As noted above, in some cases, marking 204C is used to represent the location of the vessel puncture site. In other cases, marking 204C, marking 202, and the intersection point 206 is used together to represent the location of the vessel puncture site. In some examples, the clinician would use these markings to apply pressure at the marking 204C in the direction of the markings 204A, 204B such that the puncture site is compressed between the clinician's hand and the head of the femoral bone of the patient 106.

While both markings 204A, 204B are shown, in some cases, only marking 204A or marking 204B is explicitly drawn on the skin of the patient 106, depending on the orientation of the adjustable radiography template device as described in further detail with reference to FIGS. 3A and 3B.

Figure 3A:
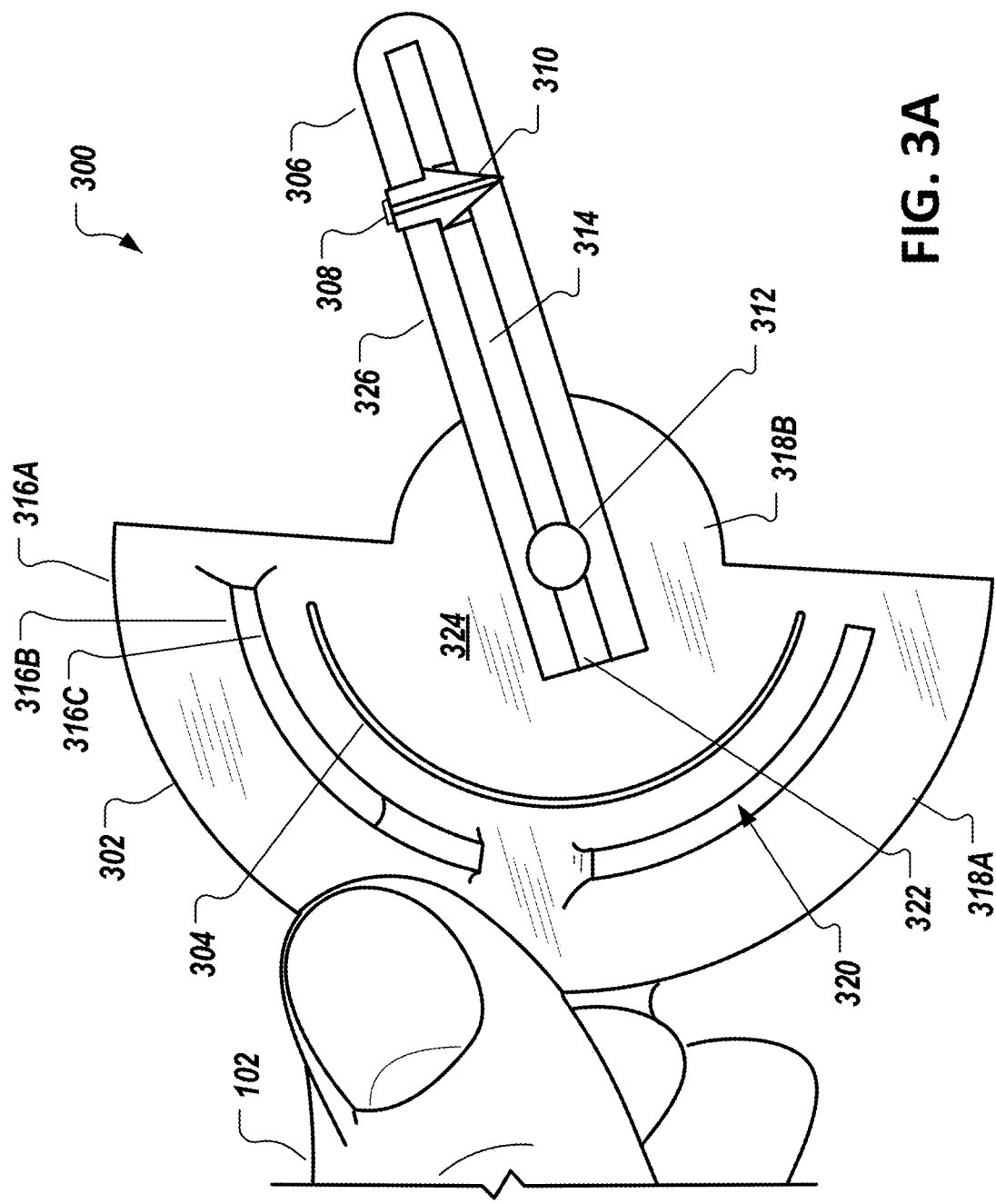
FIGS. 3A and 3B show views of an adjustable radiography template device.
Figure 3B:
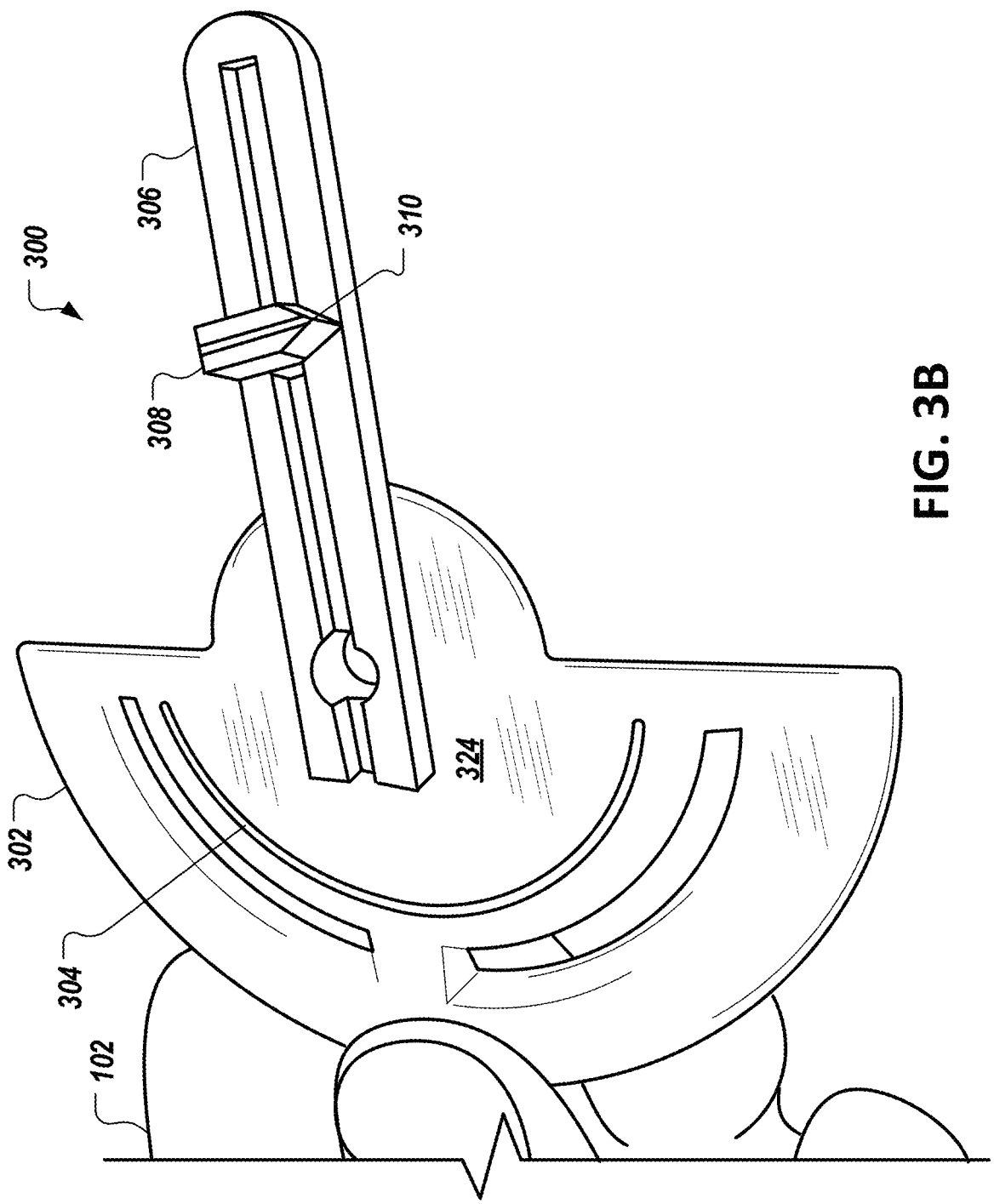

FIGS. 3A and 3B show views of an example adjustable radiography template device 300 being used by the clinician 102. In some implementations, some of the components of the adjustable radiography template device 300 comprise a plastic material such as a molded or 3D printed plastic material such that it is inexpensive to manufacture and is disposable (e.g., a single use device). In other implementations, the adjustable radiography template device 300 is manufactured from a metal such as aluminum or stainless steel and is sterilizable and reusable (e.g., a multi-use device). In some implementations, the adjustable radiography template device 300 is initially sterile and contained in sterile packaging (not shown) for shipment and storage.

The adjustable radiography template device 300 includes a base member 302 with a radiopaque (RO) marker 304. While one RO marker 304 is shown, in some implementations, the base member 302 includes more than one RO marker 304 (e.g., two, three, four, etc.). In some examples, the RO marker 304 is used to locate the head of the femoral bone of the patient 106.

The RO marker 304 is at least partially opaque to x-rays from the fluoroscopy system 104 and are therefore at least partially visible in an x-ray image shown on the display 108. In general, the adjustable radiography template device 300 is radio transparent except for the RO markers. In this way, the remainder of the adjustable radiography template device 300 (e.g., everything that is not an RO marker) is generally invisible in the x-ray image while the RO marker 304 is visible. In other words, the remainder of the adjustable radiography template device 300 is at least relatively more radio transparent than the RO marker 304.

In some implementations, the RO marker 304 is a copper wire. In some cases, the copper wire is disposed in a recess defined by the base member 302. In some cases, the recess is a semi-circular arc. In some cases, the one or more first RO markers 304 define a radiopaque arc (e.g., a semi-circular arc). In some cases, the pivot axis 312 is located at a radial center of the radiopaque arc.

In some implementations, the RO marker 304 is arranged (located on a surface, located within in a recess, etc.) in a first semi-circular portion 318A of the base member 302. The base member 302 also includes a second semi-circular portion 318B that spans the pivot axis 312. In some cases, a radial center of the semi-circular portions 318A, 318B and/or the base member 302 define the location of the pivot axis 312. In some cases, a radial center of the semi-circular portions 318A, 318B define the location of the pivot axis 312. In some cases, a radial outer diameter of the first semi-circular portion 318A is greater than a radial outer diameter of the second semi-circular portion 318B. In some cases, an outer diameter of the semi-circular portion 318A is concentric with a radiopaque arc defined by the RO markers 304.

In some implementations, the base member 302 includes multiple edges 316A, 316B, 316C (generally 316) defining an arc. In some examples, edges 316 are used as a guide to mark a location on the skin of the patient 106 representing the location of the head of the femoral bone of the patient 106. In some cases, the multiple edges 316 of the base member 302 are concentric with a radiopaque arc defined by the RO marker 304.

In some implementations, the base member 302 includes one or more openings 320 passing through the base member 302. In some cases, the openings are defined by the edges 316 such that the openings can be used as a stencil for marking (e.g., using a marking pen) the location on the skin of the patient 106 representing the location of the head of the femoral bone of the patient 106. In some cases, the base member 302 includes two openings 320 with each defining an opening in the shape of an arc.

In some implementations, an entire side of the base member 302 is flat. For example, in some cases, an entire side face 324 and/or an entire side face opposite the side face 324 is flat.

The adjustable radiography template device 300 includes an arm 306 pivotally coupled (e.g., via the pivot axis 312) to the base member 302. In some examples, the pivotal coupling is a pin allowing rotation between the arm 306 and the base member 302. The arm 306 is offset (e.g., in a direction of the pivot axis) from the base member 302 such that the arm 306 is allowed to pivot via the pivot axis 312 in a 360 degree rotation around the base member 302 (e.g., relative to the base member 302).

In some implementations, a length of the arm 306 is equal to a radial outer dimension of the base member 302. In some cases, the second semi-circular portion 318B supports the arm 306 via a frictional sliding engagement.

The adjustable radiography template device 300 includes a marker member 308 slidably coupled to the arm 306. In some implementations, the marker member 308 is slidably coupled to the arm 306 via a longitudinal track 314 of the arm 306. In some implementations, the marker member 308 is removable from the arm 306 via an end 322 of a longitudinal track 314 of the arm 306. In some implementations, the marker member 308 retains its position along the arm 306 by frictional engagement between the marker member 308 and the arm 306. The arm 306 includes multiple edges 326 that are used as a guide for marking a location on the skin of the patient 106 representing the puncture site of the femoral artery of the patient 106.

The marker member 308 includes an RO marker 310 such that the RO marker 310 moves and slides with the marker member 308 as the arm 306 revolves around the pivot axis 312 and the marker member 308 slides along the longitudinal track 314. In some implementations, the material of the RO marker 310 is the same as, or similar, to marker 304. The RO marker 310 is at least partially radiopaque such that the RO marker 310 is visible on the x-ray image shown on the display 108. In this way, the clinician 102 can refer to the x-ray image to align the location of the RO marker 310 as shown on the x-ray image with the puncture site of the blood vessel.

In some implementations, the RO marker 310 is a copper wire (or other radiopaque material) that projects away from a surface of the marker member 308 such that the copper wire can be used as a handle by the clinician 102 for sliding the marker member 308 along the longitudinal track 314 when aligning the RO marker 310 with the puncture site.

In some implementations, the base member 302, the arm 306, and the marker member 308 are radio transparent.

Figure 4:
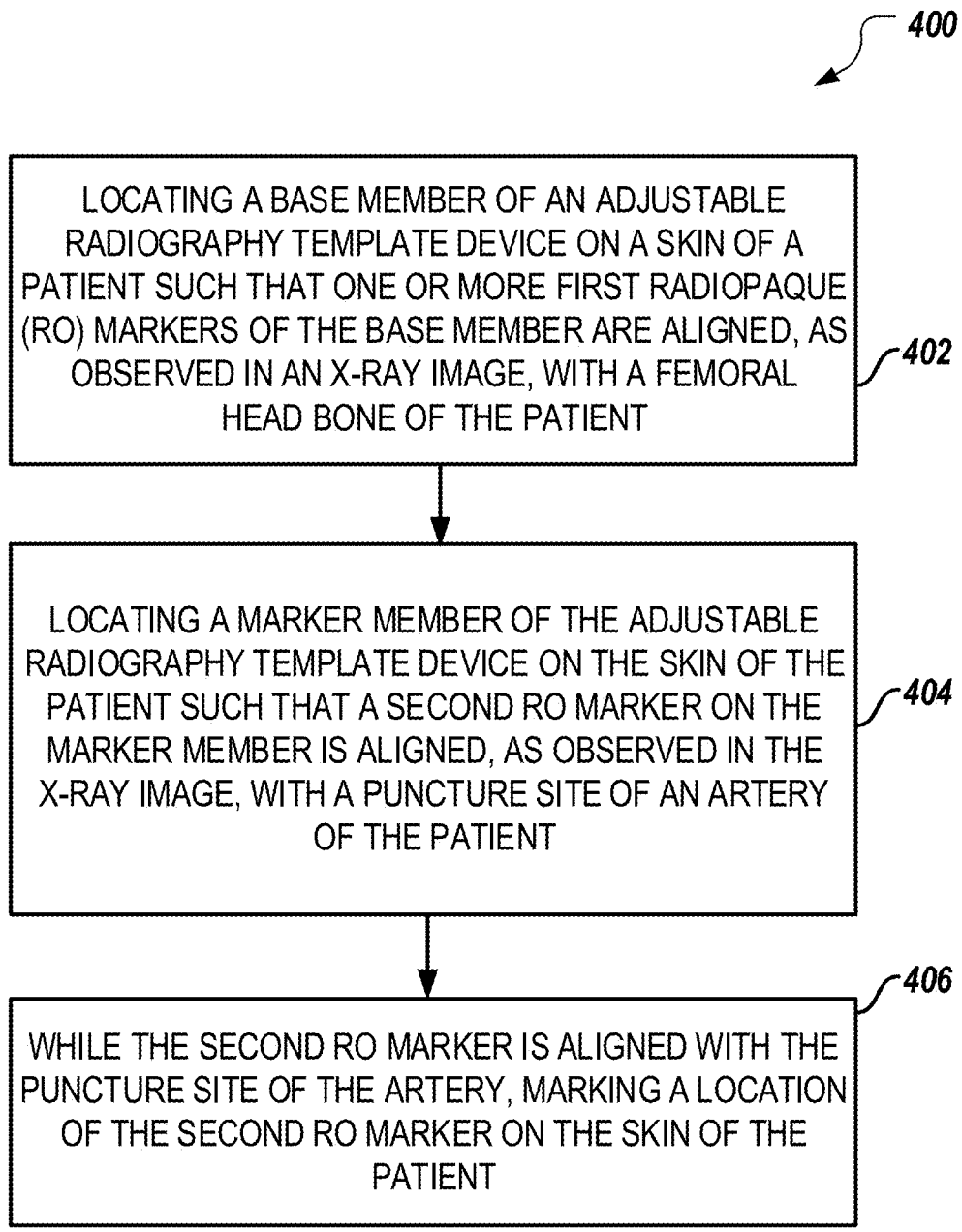
FIG. 4 illustrates a method for using an adjustable radiography template device.

FIG. 4 illustrates an example method 400 of using an adjustable radiography template device. In some implementations, the clinician 102 and/or a trained clinician perform the method 400. The method 400 includes, at step 402, locating the base member 302 of the adjustable radiography template device 300 (as described above in reference to FIGS. 3A and 3B) on a skin of a patient 106 such that one or more first RO markers 304 of the base member 302 are aligned, as observed in an x-ray image (e.g., the x-ray image 112), with a head of a femoral bone of the patient 106. The details of method 400 are further explained with reference to FIGS. 5A and 5B.

Figure 5A:
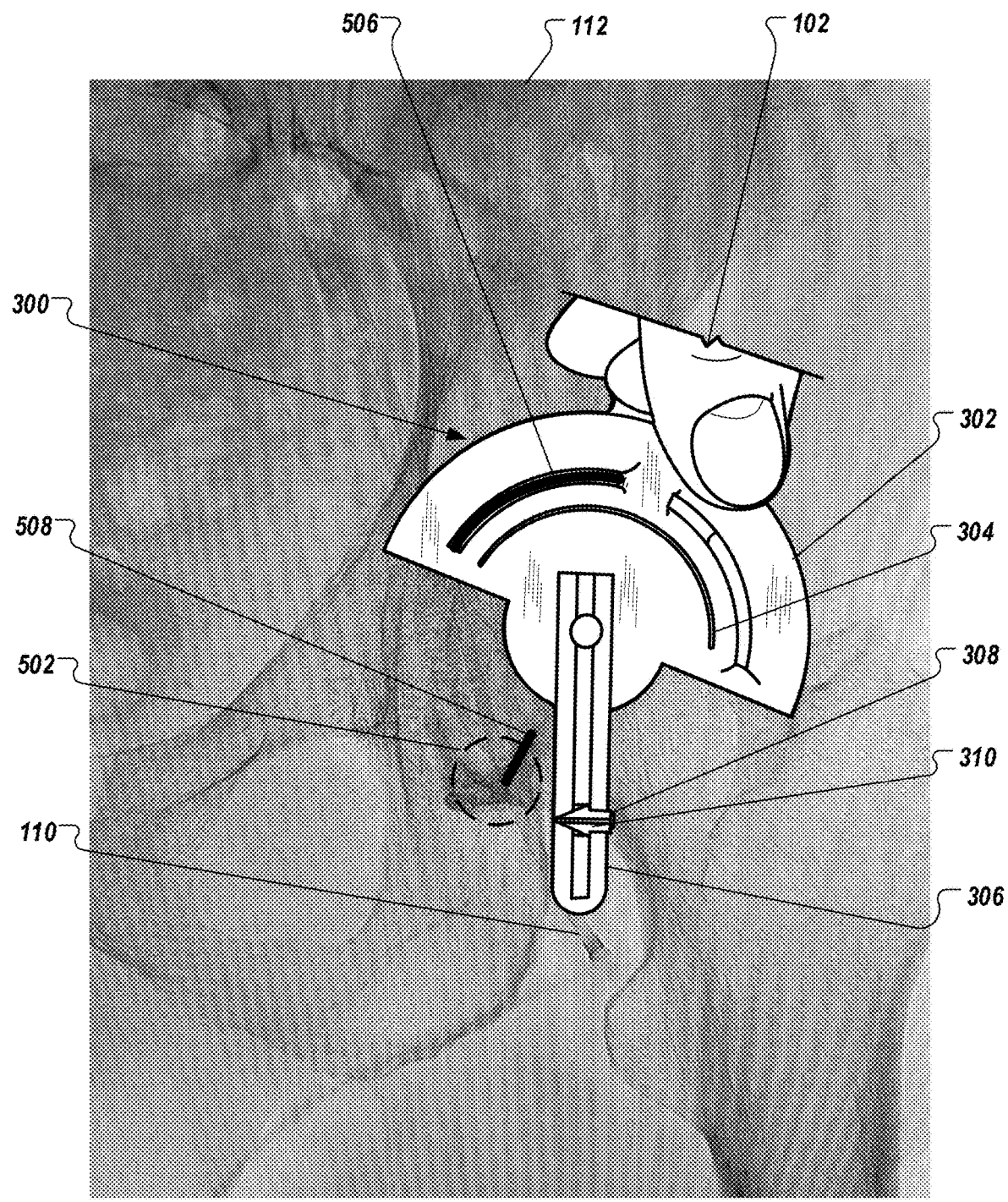
FIGS. 5A and 5B show fluoroscopy images acquired during an invasive vascular medical procedure.
Figure 5B:
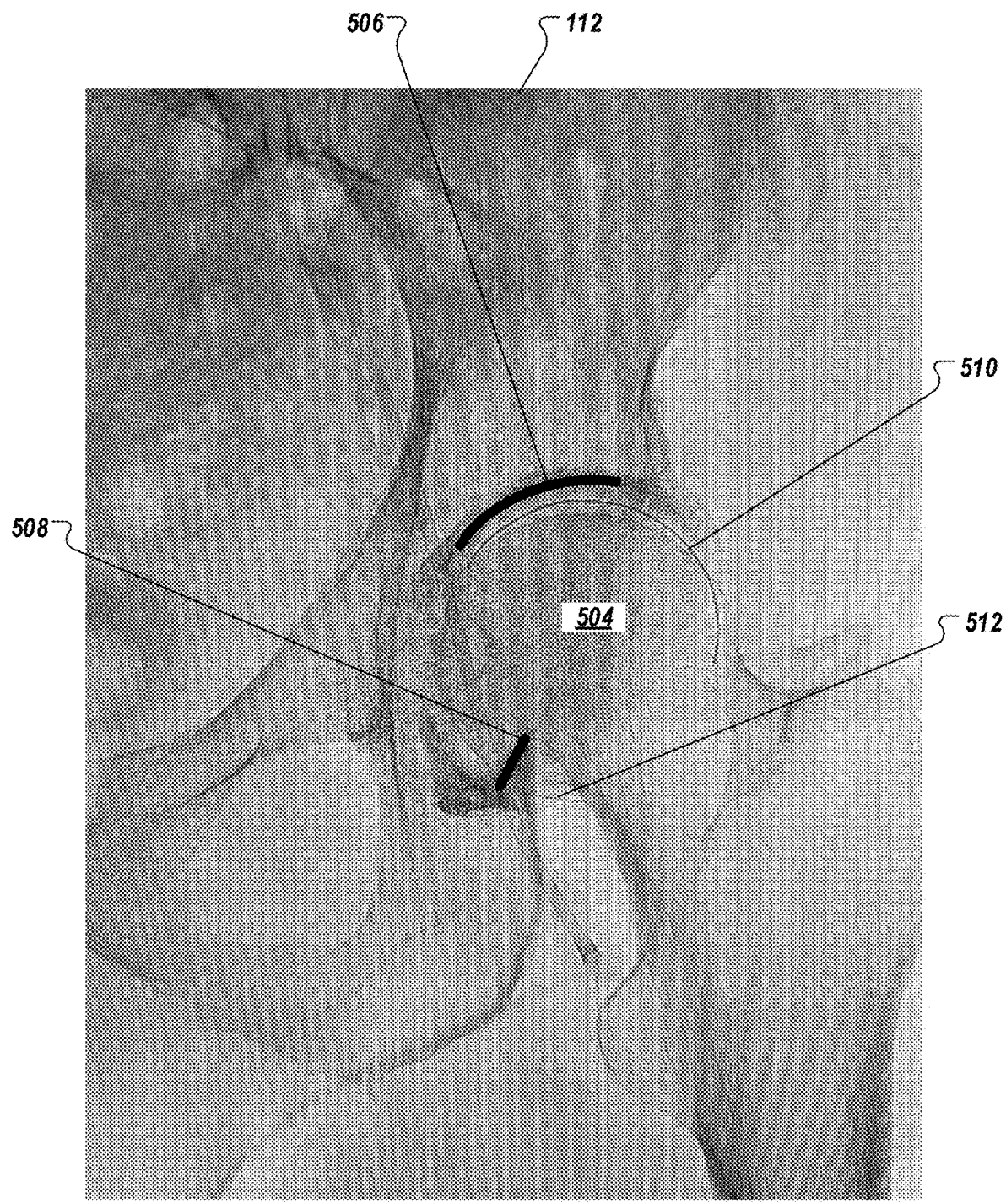

Referring also to FIGS. 5A and 5B, x-ray images 112 of the patient 106 are acquired during an invasive procedure described with reference to FIG. 1 and method 400. FIG. 5A shows the x-ray image 112 with a photo of the adjustable radiography template device 300 superimposed thereon, and FIG. 5B shows the x-ray image 112 without the adjustable radiography template device 300 superimposed (but with the adjustable radiography template device 300 in position such that the RO markers 304 are approximating the outer profile of the head of the femoral bone.

The x-ray image 112 (FIG. 5A) shows the sheath 110 as the sheath 110 extends into the femoral artery (e.g., toward the heart of the patient 106). The x-ray image 112 shows the head of the femoral bone 504 (see FIG. 5B) of the patient 106 and the vessel puncture site 502 where the sheath 110 enters the femoral artery of the patient 106. In the example shown, the sheath 110 bends at the puncture site 502 when entering the artery. In the superimposed image of FIG. 5A, the RO marker 304 of the base member 302 is shown aligned with the rim of the head of the femoral bone 504 of the patient 106.

In some implementations, locating the base member 302 of the adjustable radiography template device 300 on the skin of the patient 106 includes guiding an alignment of the one or more first RO markers 304 with the head of the femoral bone 504 of the patient 106 using fluoroscopy.

Still referring to FIG. 4, in some implementations, the method 400 includes at step 402, while the one or more first RO markers 304 are aligned with the head of the femoral bone 504 of the patient 106, marking a location 506 (as shown in FIGS. 5A and 5B) of the base member 302 on the skin of the patient 106. In some cases, marking the location 506 of the base member 302 on the skin of the patient 106 includes marking one or more arcs on the skin of the patient 106 using one or more edges 316 of the base member 302 as a guide. In some implementations, marking the location 506 of the base member 302 on the skin of the patient 106 comprises marking one or more arcs through one or more openings 320 in the base member 302.

The method 400 also includes, at step 404, locating the marker member 308 of the adjustable radiography template device 300 on the skin of the patient 106 such that a second RO marker 310 on the marker member 308 is aligned, as observed in the x-ray image 112, with the puncture site 502 of the blood vessel of the patient 106.

In some implementations, locating the marker member 308 of the adjustable radiography template device 300 on the skin of the patient 106 includes guiding an alignment of the second RO marker 310 with the puncture site 502 of the artery of the patient 106 using fluoroscopic guidance (fluoroscopy). In some implementations, locating the marker member 308 of the adjustable radiography template device 300 on the skin of the patient 106 includes sliding the marker member 308 along a longitudinal axis of the arm 306 of the adjustable radiography template device 300. In some implementations, locating the marker member 308 of the adjustable radiography template device 300 on the skin of the patient 106 includes pivoting the marker member 308 with respect to the base member 302 of the adjustable radiography template device 300.

The method 400 also includes, at step 406, while the second RO marker 310 is aligned with the puncture site of the artery, marking a location 508 of the second RO marker 310 on the skin of the patient 106. For the illustration shown in FIG. 5A, the arm 306 of the adjustable radiography template device 300 was used (e.g., as a guide) to mark the location 508 and then pivoted away from the puncture site 502 for clarity.

In some implementations, method 400 includes capturing (e.g., via the fluoroscopy system 104) the x-ray image 112 using fluoroscopy. In some implementations, method 400 includes capturing the x-ray image 112 using an angiography medical imaging technique.

In some implementations, method 400 includes inserting a sheath 110 into the artery of the patient 106. In some implementations, method 400 includes removing the sheath 110 from the artery of the patient 106.

In some implementations, method 400 includes applying pressure to the skin of the patient 106 at the marked location of the marker member. In some implementations, applying the pressure to the skin incudes applying pressure to the skin for at least 15 minutes to increase the likelihood that proper closure of the puncture site of the blood vessel is achieved. In some implementations, applying the pressure to the skin incudes applying pressure to the skin in a direction towards the location 506 such that the puncture site of the artery is compressed between a source of the applied pressure (e.g., the clinician's hand) and the head of the femoral bone of the patient 106. These actions increase a likelihood that proper closure is achieved and that complications are reduced.

FIG. 5B shows the x-ray image 112 with the RO markers 304, 310 visible at the radiopaque arc 510 and the radiopaque line 512, respectively. During use, the clinician 102 aligns the radiopaque arc 510 to the rim of the head of the femoral bone 504 using the x-ray image 112.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An adjustable radiography template device, comprising:
    a base member comprising one or more first radiopaque (RO) markers;
    an arm pivotally coupled to the base member; and
    a marker member slidably coupled to the arm and comprising a second RO marker,
    wherein the one or more first RO markers define a radiopaque arc,
    wherein the arm is pivotally coupled to the base member via a pivot axis located at a radial center of the radiopaque arc, and
    wherein the marker member is slidably coupled to the arm via a longitudinal track of the arm.

2. The adjustable radiography template device of claim 1, wherein the base member, the arm, and the marker member are radio transparent, and wherein the one or more first RO markers and the second RO marker are copper wires.

3. The adjustable radiography template device of claim 1, wherein the base member, the arm, and the marker member are less radiopaque than the one or more first RO markers and the second RO marker.

4. The adjustable radiography template device of claim 1, wherein the base member comprises one or more edges defining an arc and the one or more edges of the base member are concentric with a radiopaque arc defined by the one or more first RO markers.

5. The adjustable radiography template device of claim 1, wherein the one or more first RO markers are arranged in a semi-circular portion of the base member, and an outer diameter of the semi-circular portion is concentric with a radiopaque arc defined by the one or more first RO markers.

6. The adjustable radiography template device of claim 5, wherein the arm is pivotally coupled to the base member at a radial center of the semi-circular portion.

7. The adjustable radiography template device of claim 1, wherein the arm is pivotally coupled to the base member at a radial center of the base member, and wherein the base member comprises one or more openings passing through the base member, and wherein an entire side of the base member is flat.

8. The adjustable radiography template device of claim 1, wherein a length of the arm is equal to a radial outer dimension of the base member, and wherein the marker member is removable from the arm via an end of a longitudinal track of the arm.

9. The adjustable radiography template device of claim 8, wherein the marker member is positionable along the arm by frictional engagement between the marker member and the arm.

10. The adjustable radiography template device of claim 1, wherein the adjustable radiography template device is sterile and contained in a sterile packaging, and wherein the adjustable radiography template device is a single use device.

11. An adjustable radiography template device, comprising:
    a base member comprising one or more first radiopaque (RO) markers defining a radiopaque arc and one or more edges defining an arc concentric with the radiopaque arc;
    an arm pivotally coupled to the base member at a pivot axis, the pivot axis located at a radial center of the radiopaque arc; and
    a marker member slidably coupled to the arm via a longitudinal track of the arm, the marker member comprising a second RO marker.

12. The adjustable radiography template device of claim 11, wherein the base member, the arm, and the marker member are less radiopaque than the one or more first RO markers and the second RO marker, and wherein the one or more first RO markers and the second RO marker are copper wires.

13. The adjustable radiography template device of claim 11, wherein the marker member is positionable along the arm by frictional engagement between the marker member and the arm.

14. An adjustable radiography template device, comprising:
    a base member comprising one or more first radiopaque (RO) markers;
    an arm pivotally coupled to the base member; and
    a marker member slidably coupled to the arm and comprising a second RO marker,
    wherein the base member comprises one or more edges defining an arc and the one or more edges of the base member are concentric with a radiopaque arc defined by the one or more first RO markers.

15. The adjustable radiography template device of claim 14, wherein the base member, the arm, and the marker member are radio transparent, and wherein the one or more first RO markers and the second RO marker are copper wires.

16. The adjustable radiography template device of claim 14, wherein a length of the arm is equal to a radial outer dimension of the base member, and wherein the marker member is removable from the arm via an end of a longitudinal track of the arm.

17. An adjustable radiography template device, comprising:
    a base member comprising one or more first radiopaque (RO) markers;
    an arm pivotally coupled to the base member; and
    a marker member slidably coupled to the arm and comprising a second RO marker,
    wherein the one or more first RO markers are arranged in a semi-circular portion of the base member, and an outer diameter of the semi-circular portion is concentric with a radiopaque arc defined by the one or more first RO markers.

18. The adjustable radiography template device of claim 17, wherein the arm is pivotally coupled to the base member at a radial center of the semi-circular portion.

19. The adjustable radiography template device of claim 17, wherein the base member, the arm, and the marker member are radio transparent, and wherein the one or more first RO markers and the second RO marker are copper wires.

20. The adjustable radiography template device of claim 17, wherein a length of the arm is equal to a radial outer dimension of the base member, and wherein the marker member is removable from the arm via an end of a longitudinal track of the arm.

\* \* \* \* \*